United States Patent
Lee et al.

(10) Patent No.: US 11,547,379 B2
(45) Date of Patent: Jan. 10, 2023

(54) METHOD AND APPARATUS FOR SCATTER ARTIFACTS CORRECTION IN INDUSTRIAL 3-DIMENSIONAL CONE BEAM COMPUTED TOMOGRAPHY

(71) Applicant: Korea Advanced Institute of Science and Technology, Daejeon (KR)

(72) Inventors: Chang-Ock Lee, Daejeon (KR); Soomin Jeon, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 101 days.

(21) Appl. No.: 17/217,452

(22) Filed: Mar. 30, 2021

(65) Prior Publication Data
US 2022/0079542 A1 Mar. 17, 2022

(30) Foreign Application Priority Data
Sep. 11, 2020 (KR) .......... 10-2020-0116509

(51) Int. Cl.
*A61B 6/00* (2006.01)
*A61B 6/03* (2006.01)
(52) U.S. Cl.
CPC .......... *A61B 6/5282* (2013.01); *A61B 6/032* (2013.01); *A61B 6/5205* (2013.01)

(58) Field of Classification Search
CPC ..... A61B 6/5282; A61B 6/032; A61B 6/5205; G06T 11/003; G06T 2207/10076; G06T 2211/416; G06F 17/10
See application file for complete search history.

(56) References Cited

U.S. PATENT DOCUMENTS

2010/0208870 A1* 8/2010 Zou .......... A61B 6/032
382/131

FOREIGN PATENT DOCUMENTS

JP 2020116377 A 8/2020

OTHER PUBLICATIONS

Jeon et al. "A Shape prior metal artefact reduction algorithm for industrial 3D cone beam CT," 20 pages, Nondestructive Testing and Evaluation, Jan. 3, 2020.

* cited by examiner

*Primary Examiner* — Courtney D Thomas
(74) *Attorney, Agent, or Firm* — PCFB LLC

(57) ABSTRACT

Provided are a method and apparatus for correcting scattering artifacts in industrial three-dimensional (3D) cone beam computed tomography (CT) that may prepare raw data acquired from a subject through computed tomography (CT) and a primary signal acquired from shape prior information of the subject, may estimate a scatter kernel based on the raw data and the primary signal, may acquire result data by removing, from the raw data, a scatter signal estimated based on the scatter kernel, and may generate an image from the result data.

20 Claims, 19 Drawing Sheets

FIG. 3

```
For k=1:Generations
        p=Particle_Reinitialization(gBest, range)
        For i=1:it_max
            For each particle p in P do
                fp=evaluation of ( ) at p
                If fp is better than f(pBest)
                    pBest=p;
                END
            END
            gbest=best p in P
            For each particle p in P do
                v= v+c1*rand*(pBest-p)+c2*rand*(gBest-p)
                p=p+v
            End
        End
End
```

METHOD AND APPARATUS FOR SCATTER ARTIFACTS CORRECTION IN INDUSTRIAL 3-DIMENSIONAL CONE BEAM COMPUTED TOMOGRAPHY

CROSS-REFERENCE TO RELATED APPLICATION

This application claims the priority benefit of Korean Patent Application No. 10-2020-0116509, filed on Sep. 11, 2020, in the Korean Intellectual Property Office, the disclosure of which is incorporated herein by reference in its entirety.

BACKGROUND

1. Field of the Invention

The following description of example embodiments relates to a method and apparatus for correcting scattering artifacts occurring in industrial three-dimensional (3D) cone beam computed tomography (CT).

2. Description of the Related Art

X-ray computed tomography (X-ray CT) is one of imaging techniques most widely used in medical and industrial fields. To reconstruct an image, a scattering effect that degrades an image quality is included in raw data acquired from an actual device. There is a research result that this may be represented through a scatter kernel. However, since there is no method of efficiently calculating a scatter kernel within a given time and analysis about accuracy of variables that determine the scatter kernel is not guaranteed, there are some limitations to use in an actual field.

SUMMARY

Example embodiments provide an electronic device for correcting scattering artifacts in industrial three-dimensional (3D) cone beam computed tomography (CT) and an operating method of the electronic device.

Example embodiments provide an electronic device that may remove, from raw data, a scatter signal estimated based on a scatter kernel by efficiently estimating the scatter kernel and an operating method of the electronic device.

According to an aspect of example embodiments, there is provided an operating method of an electronic device including preparing raw data acquired from a subject through computed tomography (CT) and a primary signal acquired from shape prior information of the subject; estimating a scatter kernel based on the raw data and the primary signal; acquiring result data by removing, from the raw data, a scatter signal estimated based on the scatter kernel; and generating an image from the result data.

According to an aspect of example embodiments, there is provided an electronic device including a data preparation module configured to prepare raw data acquired from a subject through CT and a primary signal acquired from shape prior information of the subject; a scatter artifacts correction module configured to estimate a scatter kernel based on the raw data and the primary signal and to acquire result data by removing, from the raw data, a scatter signal estimated based on the scatter kernel; and an image generation module configured to generate an image from the result data.

According to an aspect of example embodiments, there is provided a non-transitory computer-readable record medium storing at least one program to perform a method including preparing raw data acquired from a subject through CT and a primary signal acquired from shape prior information of the subject; estimating a scatter kernel based on the raw data and the primary signal; acquiring result data by removing, from the raw data, a scatter signal estimated based on the scatter kernel; and generating an image from the result data.

According to some example embodiments, an electronic device may efficiently estimate a scatter kernel by accurately estimating variables used to determine the scatter kernel. That is, the electronic device may efficiently estimate the scatter kernel without an additional physical operation. In this manner, the electronic device may effectively correct a scattering effect, that is, scattering artifacts occurring in CT by removing a scatter signal from raw data. That is, the electronic device may generate a clear CT image that does not include the scattering effect.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

These and/or other aspects, features, and advantages of the invention will become apparent and more readily appreciated from the following description of embodiments, taken in conjunction with the accompanying drawings:

FIG. 3 illustrates an example of an operation algorithm of the scatter artifacts correction module of FIG. 1;

DETAILED DESCRIPTION

Figure 1:
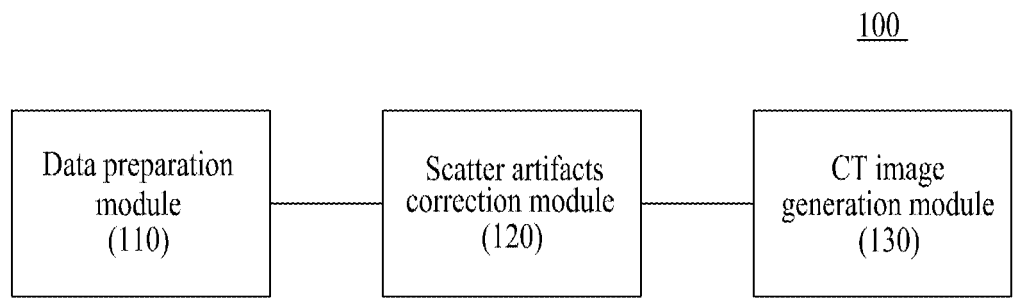
FIG. 1 is a diagram illustrating an example of an electronic device according to example embodiments.

One or more example embodiments will be described in detail with reference to the accompanying drawings. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments.

When a component is described to be on another component, the component may be directly formed on the other component or a third component may be provided between the components. Also, in the drawings, thicknesses of components may be exaggerated to effectively describe technical content. Unless otherwise noted, like reference numerals refer to like components throughout the attached drawings and written description, and thus descriptions will not be repeated.

The example embodiments described herein will be described with the accompanying drawings. In the drawings, thicknesses of layers, regions, etc., may be exaggerated for effective description of the technical content. Accordingly, regions illustrated in the drawings may have general attributes and shapes of the regions are merely provided as examples and not construed to limit the scope of the disclosure.

Hereinafter, the example embodiments are described with reference to the accompanying drawings.

Figure 2:
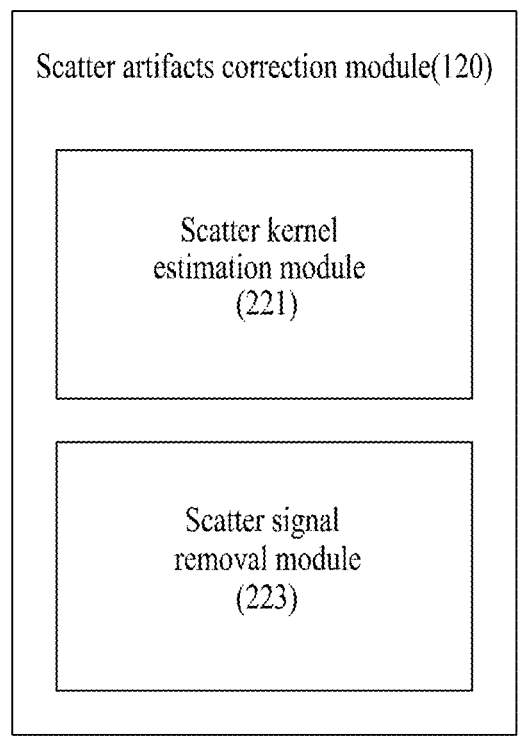
FIG. 2 is a diagram illustrating an example of a scatter artifacts correction module of FIG. 1.

FIG. 1 is a diagram illustrating an example of an electronic device 100 according to example embodiments, FIG. 2 is a diagram illustrating an example of a scatter artifacts correction module 120 of FIG. 1, and FIG. 3 illustrates an example of an operation algorithm of the scatter artifacts correction algorithm 120 of FIG. 1.

Referring to FIG. 1, the electronic device 100 may include a data preparation module 110, the scatter artifacts correction module 120, and a computed tomography (CT) image generation module 130.

The data preparation module 110 may prepare raw data (contaminated raw data) that includes a scattering effect, for example, scattering artifacts and a primary signal. The raw data may include the scattering effect as CT data that is acquired from a subject through CT. The primary signal may be generated from shape prior information of the subject. The shape prior information may be acquired using various methods. For example, the shape prior information may be computer-aided design (CAD) data and the primary signal may be generated from the CAD data.

The scatter artifacts correction module 120 may correct the scattering effect in the raw data. To this end, a minimization problem as in the following Equation 1 may be defined. According to the following Equation 1, a scatter kernel may be associated with multiple variables and may be determined based on these variables. Here, a spatial Gaussian kernel portion of the scatter kernel may include a Compton scattering effect and a Rayleigh scattering effect occurring in the CT, and the scatter kernel may be defined as the following Equation 2. Through this, variables associated with the scatter kernel may be defined as a group represented as the following Equation 3.

$$\min_{x}\|I - (\tilde{I}_p + \tilde{I}_s)\|^2 \quad \text{[Equation 1]}$$

In Equation 1, x denotes the variables, I denotes the raw data, $\tilde{I}_p$ denotes the primary signal, and $\tilde{I}_s$ denotes a scatter signal estimated based on the scatter kernel.

$$\tilde{I}_s(x, y) = (\tilde{I}_p(x, y)A_f(x, y)) * h_s(x, y) \quad \text{[Equation 2]}$$

$$A_f = A \cdot \left(\frac{\tilde{I}_p(x, y)}{I_0(x, y)}\right)^\alpha \cdot \left(\ln\left(\frac{I_0(x, y)}{\tilde{I}_p(x, y)}\right)\right)^\beta$$

$$h_s = \left[\exp\left(\frac{-r^2}{2\sigma_1^2}\right) + B \exp\left(\frac{-r^2}{2\sigma_2^2}\right)\right]$$

$$x = (A, \alpha, \beta, \sigma_1, B, \sigma_2) \quad \text{[Equation 2]}$$

Referring to FIG. 2, the scatter artifacts correction module 120 may include a scatter kernel estimation module 221 and a scatter signal removal module 223.

The scatter kernel estimation module 221 may estimate a scatter kernel based on raw data and a primary signal. To this end, the scatter kernel estimation module 221 may separately estimate each variable associated with the scatter kernel. According to an example embodiment, the scatter kernel estimation module 221 may estimate variables in a stepwise manner. That is, the scatter kernel estimation module 221 may primarily estimate a portion of the variables and may secondarily estimate the remaining variables based on the primarily estimated variables. The scatter kernel estimation module 221 may estimate the scatter kernel based on the values of the variables. That is, the scatter kernel estimation module 221 may estimate the scatter kernel based on the values of the variables by solving the minimization problem of Equation 1.

For example, referring to FIG. 3, the scatter kernel estimation module 221 may estimate a scatter kernel using a restarted particle swarm optimization (PSO) algorithm. The restarted PSO algorithm may reinitialize particles after a certain number of iterations have been performed, which differs from a general PSO algorithm. That is, the restarted PSO algorithm may reinitialize particles by narrowing the range around gBest. Through this, the restarted PSO algorithm may improve distribution and emigration direction of particles.

The scatter signal removal module 223 may remove, from the raw data, the scatter signal estimated based on the scatter kernel. Through this, result data in which the scatter signal is removed from the raw data may be acquired.

The CT image generation module 130 may generate a CT image. That is, the CT image generation module 130 may reconstruct a CT image based on result data acquired from the scatter artifacts correction module 120. Since the result data is acquired by removing the scatter signal from the raw data, the CT image may not include the scattering effect.

Figure 4:
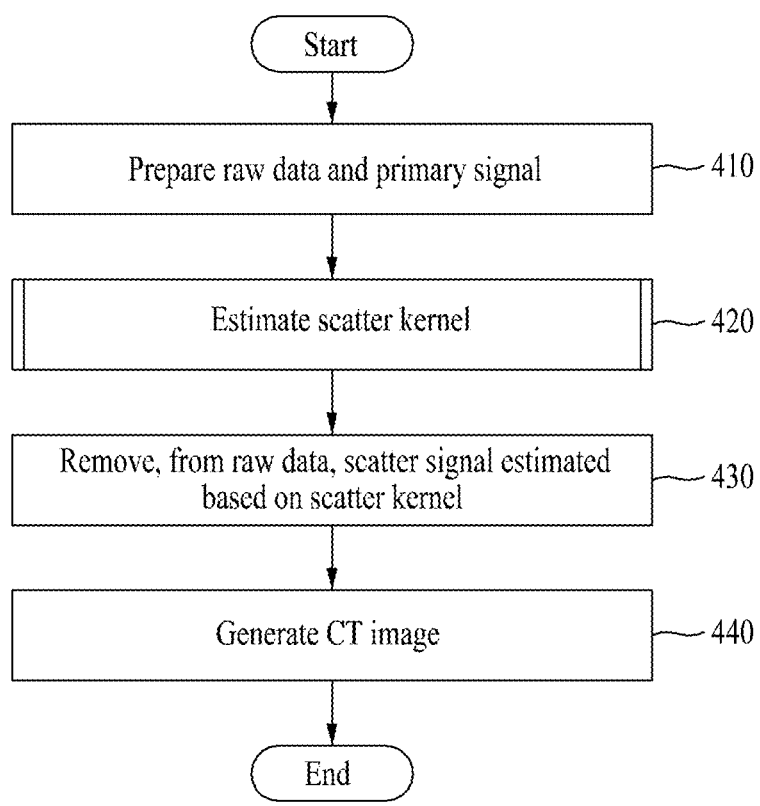
FIG. 4 is a flowchart illustrating an example of an operating method of an electronic device according to example embodiments.
Figure 5:
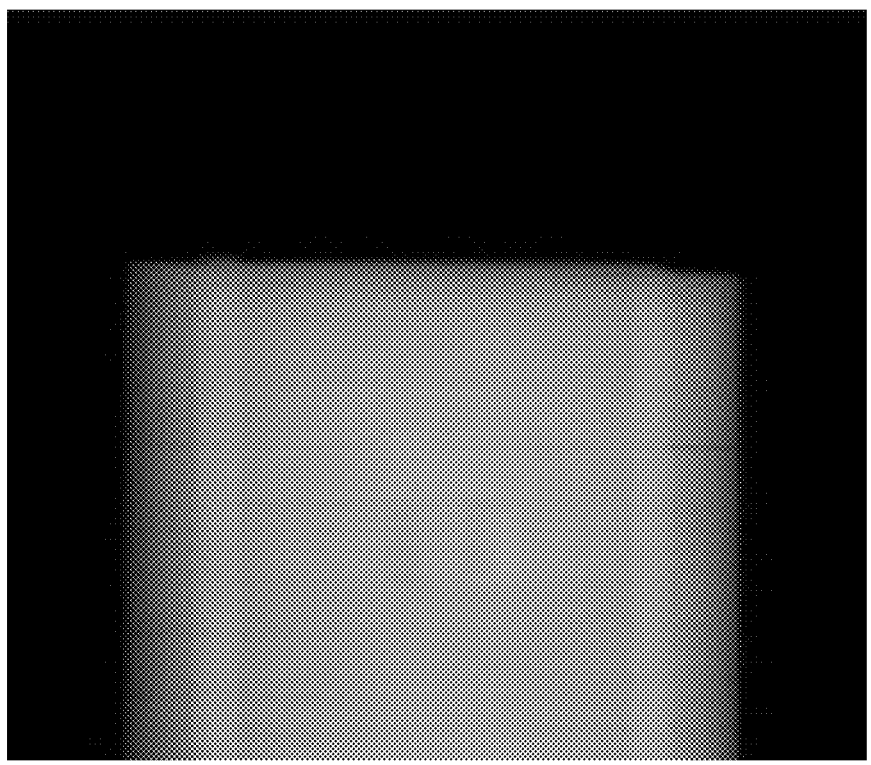
FIGS. 5, 6A, and 6B illustrate examples of describing an operation of preparing raw data and a primary signal of FIG. 4.
Figure 6A:
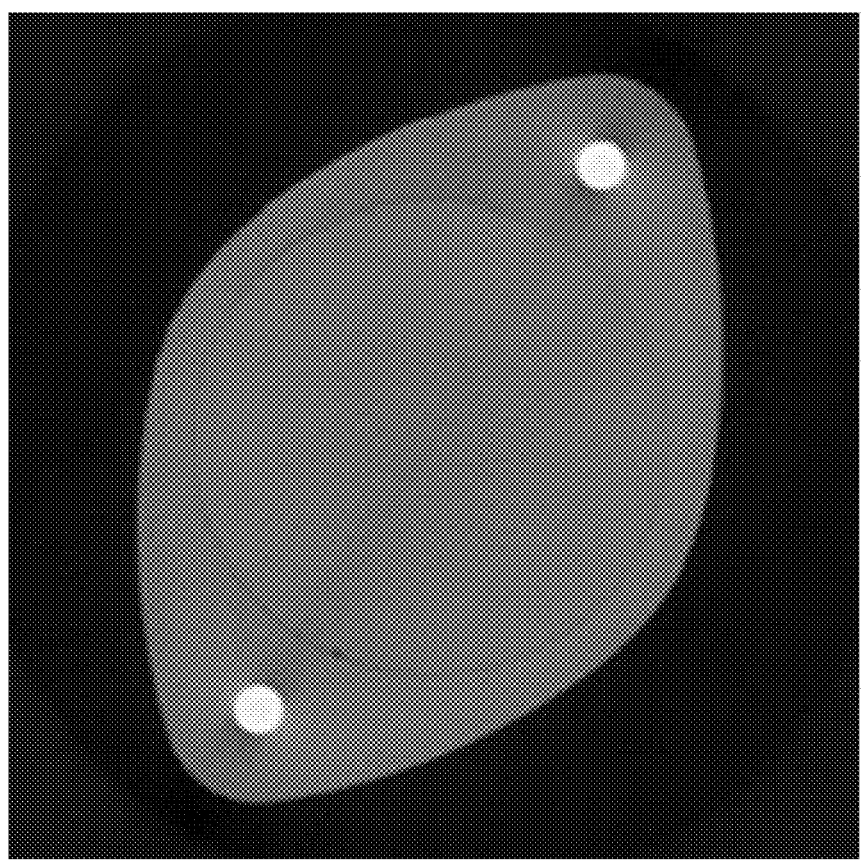
Figure 6B:
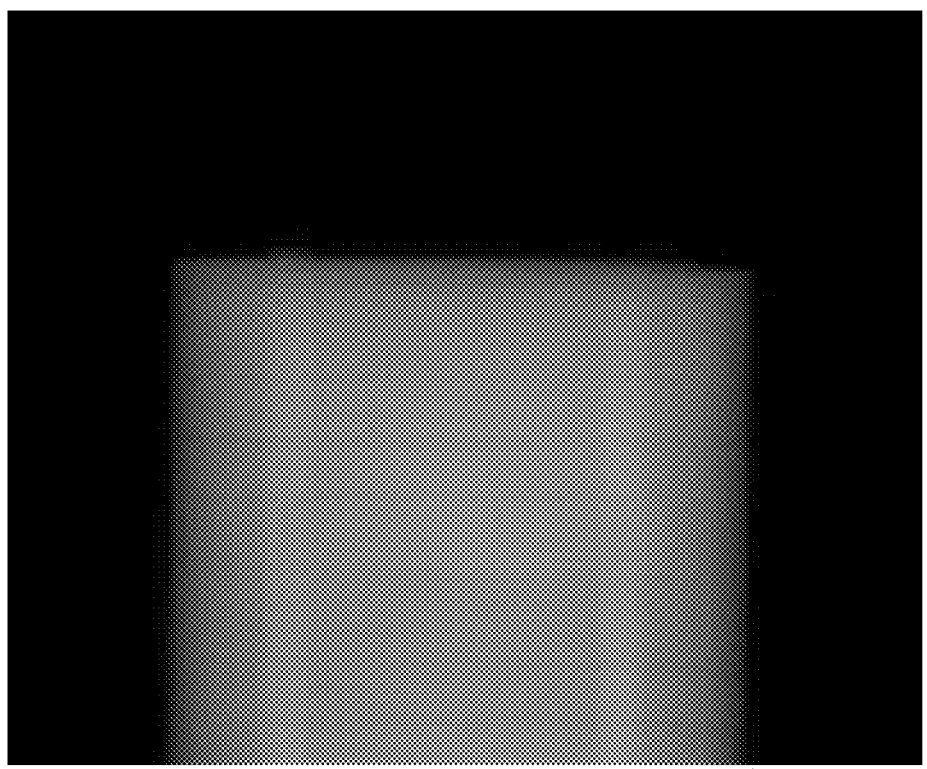

FIG. 4 is a flowchart illustrating an example of an operating method of the electronic device 100 according to example embodiments, and FIGS. 5, 6A, and 6B illustrate examples of describing an operation of preparing raw data and a primary signal of FIG. 4.

Referring to FIG. 4, in operation 410, the electronic device 100 may prepare raw data and a primary signal. The data preparation module 110 may prepare the raw data and the primary signal. The raw data may include a scattering effect as CT data acquired from a subject through CT. For example, raw data of FIG. 5 may be acquired. The primary signal may be generated from shape prior information of the subject. The shape prior information may be acquired using various techniques. For example, the shape prior information may be CAD data and the primary signal may be generated from the CAD data. For example, the shape prior information may be acquired as illustrated in FIG. 6A and, based thereon, the primary signal may be generated as illustrated in FIG. 6B.

In operation 420, the electronic device 100 may estimate a scatter kernel. To this end, a minimization problem as represented as the following Equation 4 may be defined. According to the following Equation 4, the scatter kernel may be associated with multiple variables and may be determined based on these variables. Here, a scatter signal may be estimated based on the variables associated with the scatter kernel as represented as the following Equation 5. The variables associated with the scatter kernel may be defined as a group represented as the following Equation 6.

$$\min_{x} \| I - (\tilde{I}_p + \tilde{I}_s) \|^2 \quad \text{[Equation 4]}$$

In Equation 4, x denotes the variables, I denotes the raw data, $\tilde{I}_p$ denotes the primary signal, and $\tilde{I}_s$ denotes the scatter signal estimated based on the scatter kernel.

$$\tilde{I}_s(x, y) = (\tilde{I}_p(x, y) A_f(x, y)) * h_s(x, y) \quad \text{[Equation 5]}$$

$$A_f = A \cdot \left( \frac{\tilde{I}_p(x, y)}{I_0(x, y)} \right)^{\alpha} \cdot \left( \ln\left( \frac{I_0(x, y)}{\tilde{I}_p(x, y)} \right) \right)^{\beta}$$

$$h_s = \left[ \exp\left( \frac{-r^2}{2\sigma_1^2} \right) + B \exp\left( \frac{-r^2}{2\sigma_2^2} \right) \right]$$

$$x = (A, \alpha, \beta, \sigma_1, B, \sigma_2) \quad \text{[Equation 6]}$$

The scatter artifacts correction module 120 may estimate the scatter kernel based on the raw data and the primary signal. To this end, the scatter artifacts correction module 120 may separately estimate each variable associated with the scatter kernel. According to an example embodiment, the scatter kernel estimation module 221 may estimate variables in a stepwise manner. That is, the scatter kernel estimation module 221 may primarily estimate a portion of the variables and may secondarily estimate the remaining variables based on the primarily estimated variables. To this end, the variables may include at least one sub-variable and main variables. For example, in the group of Equation 6, B and $\sigma_2$ may be sub-variables, and A, $\alpha$, $\beta$ and $\sigma_1$ may be main variables. Therefore, the scatter artifacts correction module 120 may estimate the scatter kernel based on the values of the variables. That is, the scatter artifacts correction module 120 may estimate the scatter kernel based on the values of the variables by solving the minimization problem of Equation 4. It will be further described with reference to FIG. 7.

Figure 7:
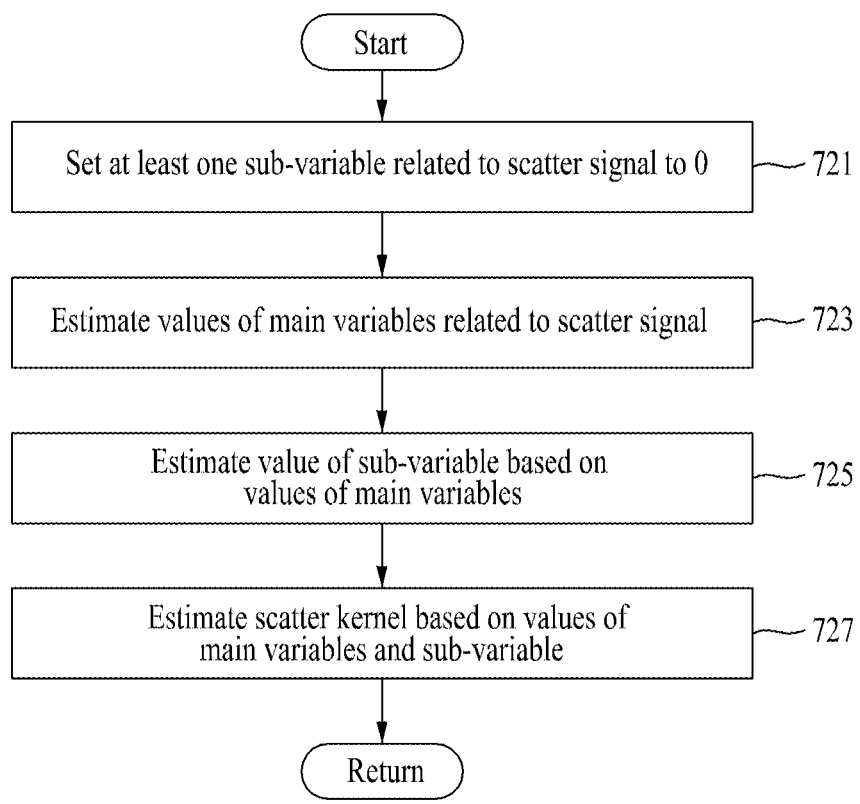
FIG. 7 is a flowchart illustrating an example of a scatter kernel estimation operation of FIG. 4.

FIG. 7 is a flowchart illustrating an example of a scatter kernel estimation operation 420 of FIG. 4.

Referring to FIG. 7, in operation 721, the scatter artifacts correction module 120 may set the value of a sub-variable to 0. For example, the scatter artifacts correction module 120 may set B to 0. In operation 723, the scatter artifacts correction module 120 may estimate main variables. For example, the scatter artifacts correction module 120 may estimate A, $\alpha$, $\beta$, and $\sigma_1$. Also, in operation 725, tge scatter artifacts correction module 120 may estimate the sub-variable based on the values of the main variables. For example, the scatter artifacts correction module 120 may estimate B and $\sigma_2$ based on values of A, $\alpha$, $\beta$, and $\sigma_1$. Therefore, in operation 727, the scatter artifacts correction module 120 may estimate the scatter kernel based on the values of the main variables and the sub-variable. The scatter artifacts correction module 120 may estimate the scatter kernel by solving the minimization problem of Equation 4. Subsequently, the scatter artifacts correction module 120 may perform operation 430 by returning to FIG. 4.

In operation 430, the electronic device 100 may remove, from the raw data, the scatter signal estimated based on the scatter kernel. The scatter artifacts correction module 120 may remove the scatter signal from the raw data. Through this, result data in which the scatter signal is removed from the raw data may be acquired.

In operation 440, the electronic device 100 may generate a CT image. The CT image generation module 130 may reconstruct the CT image based on the result data acquired from the scatter artifacts correction module 120. In detail, the CT image generation module 130 may generate a sinogram from the result data. Here, the CT image generation module 130 may generate the sinogram through a log transform on the result data. The CT image generation module 130 may reconstruct the CT image based on the sinogram. Therefore, since the result data is acquired by removing the scatter signal from the raw data, the CT image may not include the scattering effect.

Figure 8A:
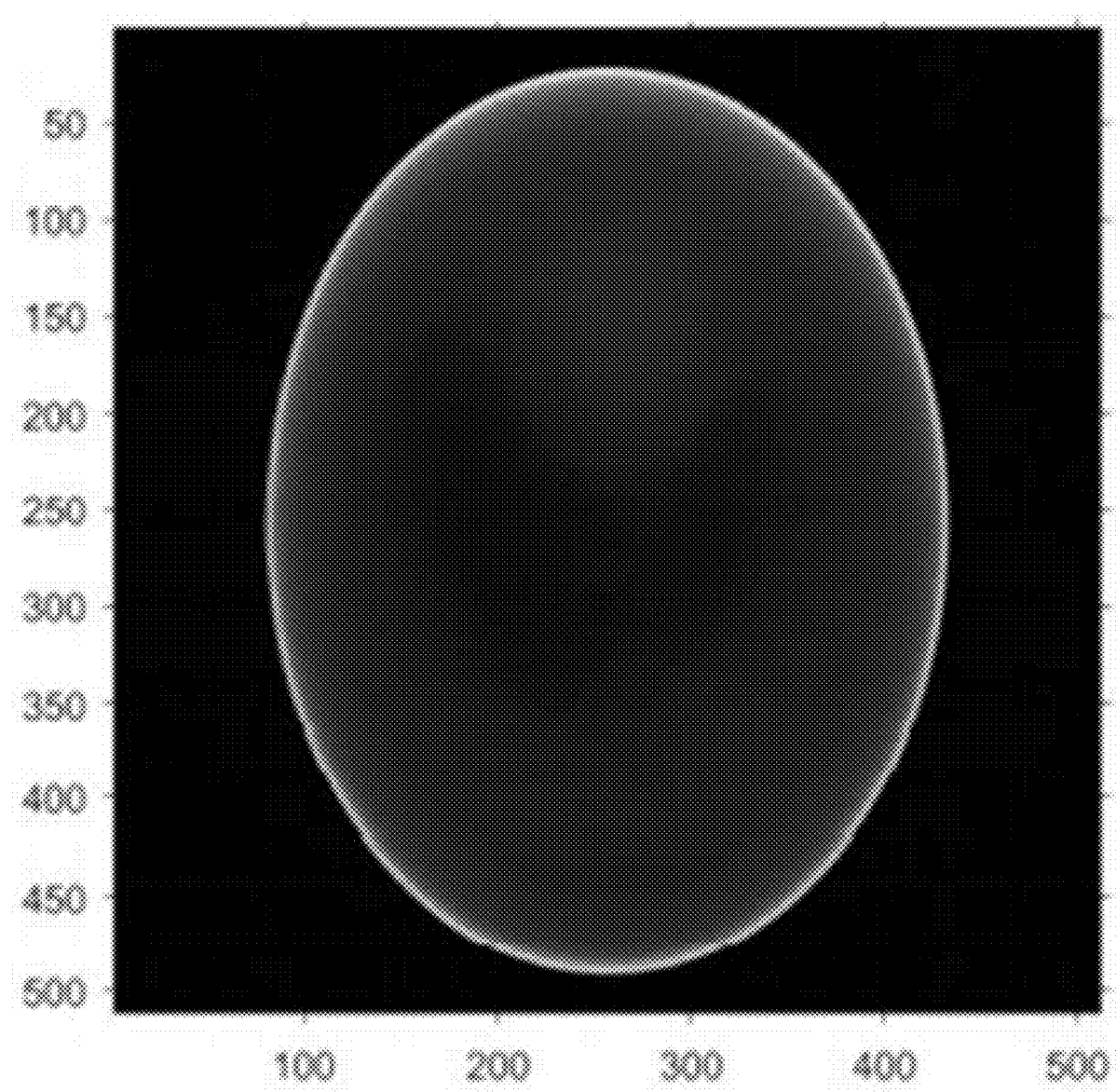
FIGS. 8A, 8B, 8C, 8D, 9A, 9B, 9C, 9D, 10A, 10B, and 10C illustrate examples of describing operation performance of an electronic device according to example embodiments.
Figure 8B:
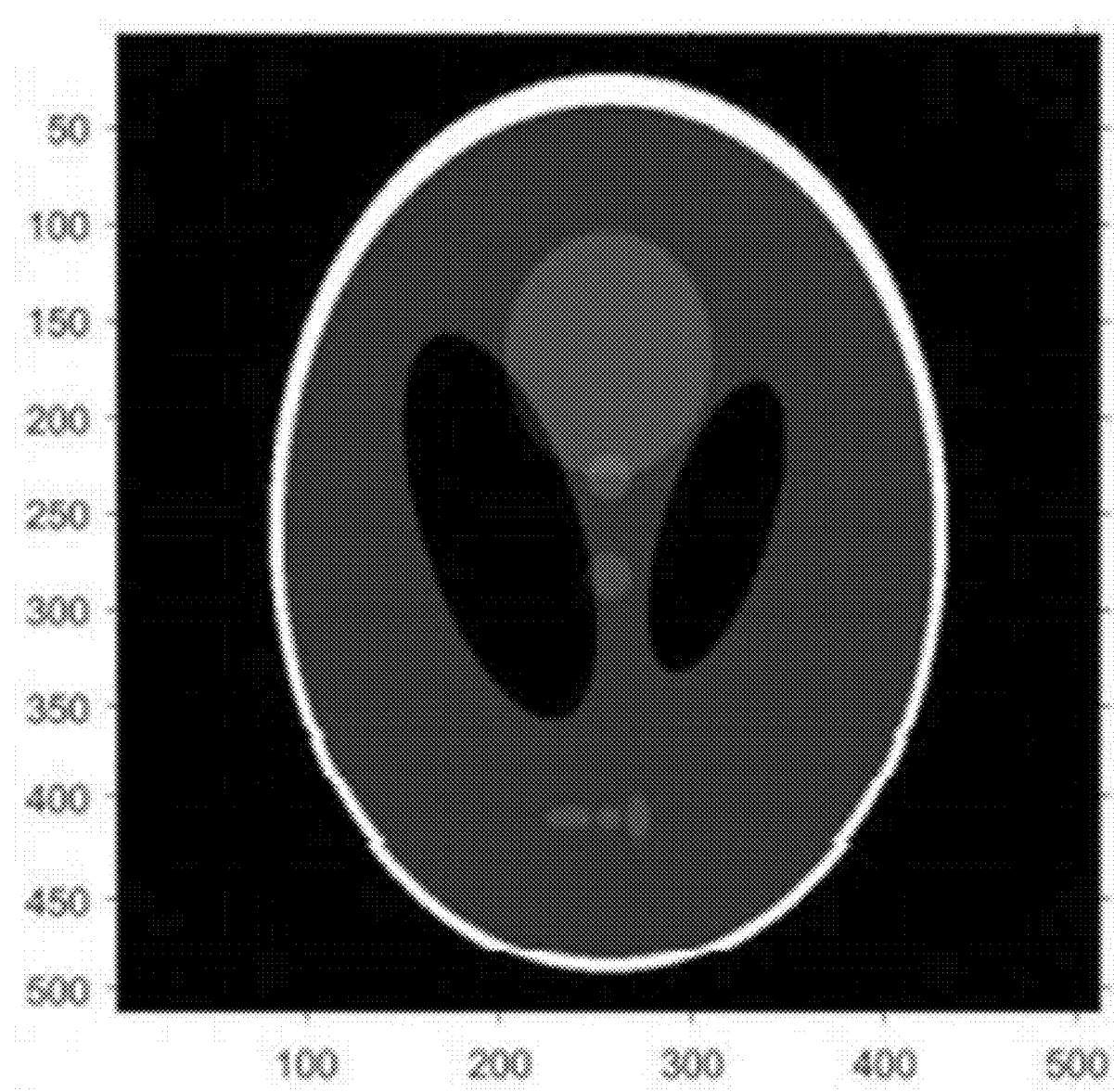
Figure 8C:
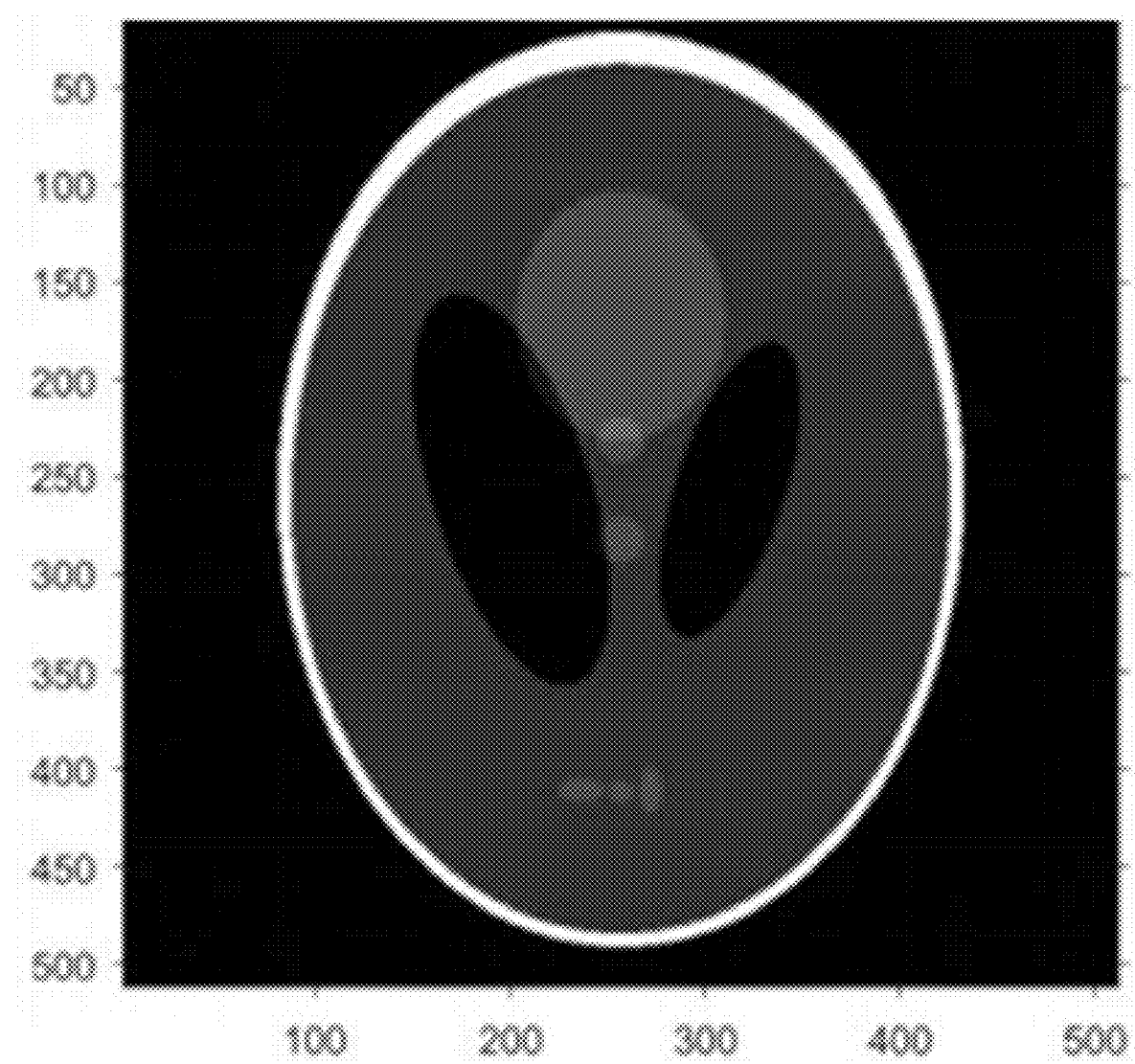
Figure 8D:
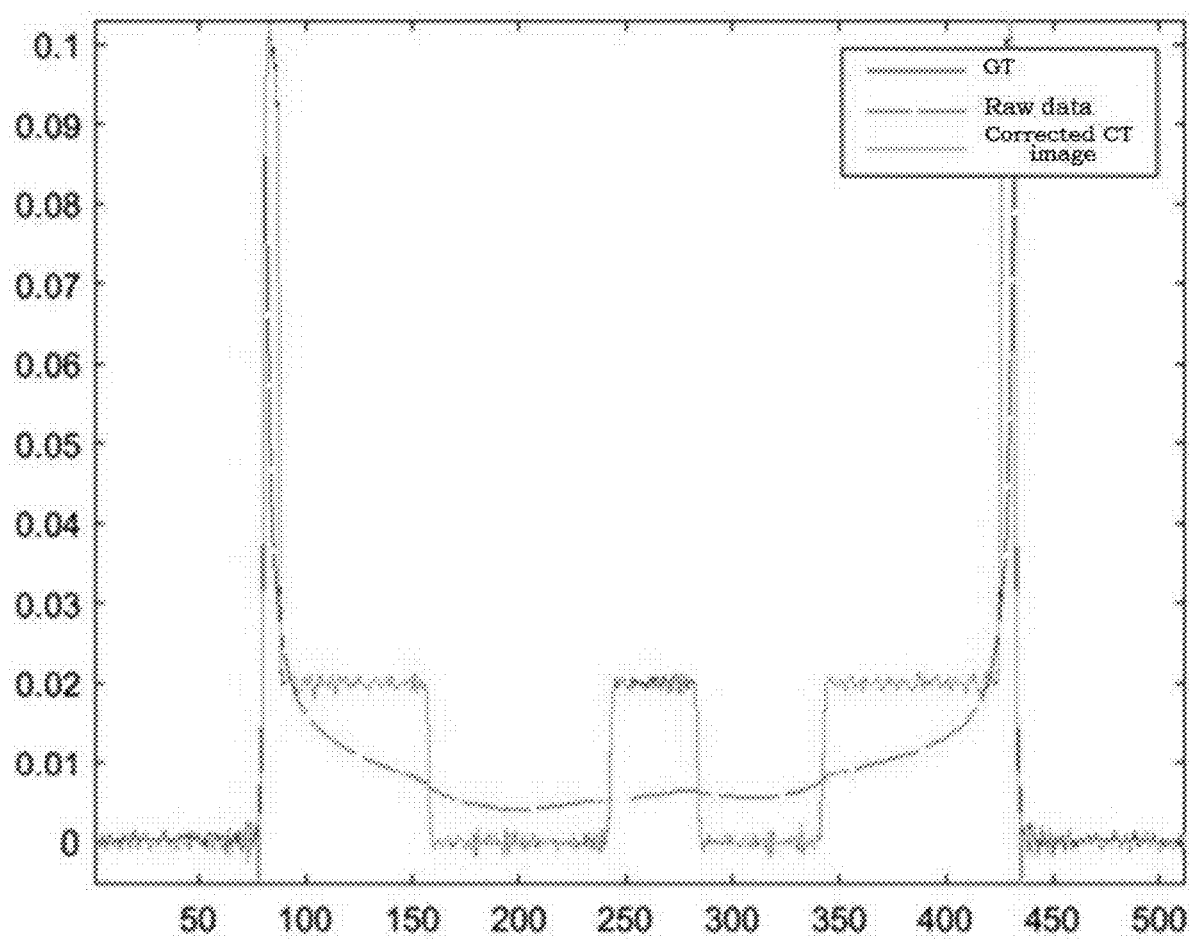
Figure 9A:
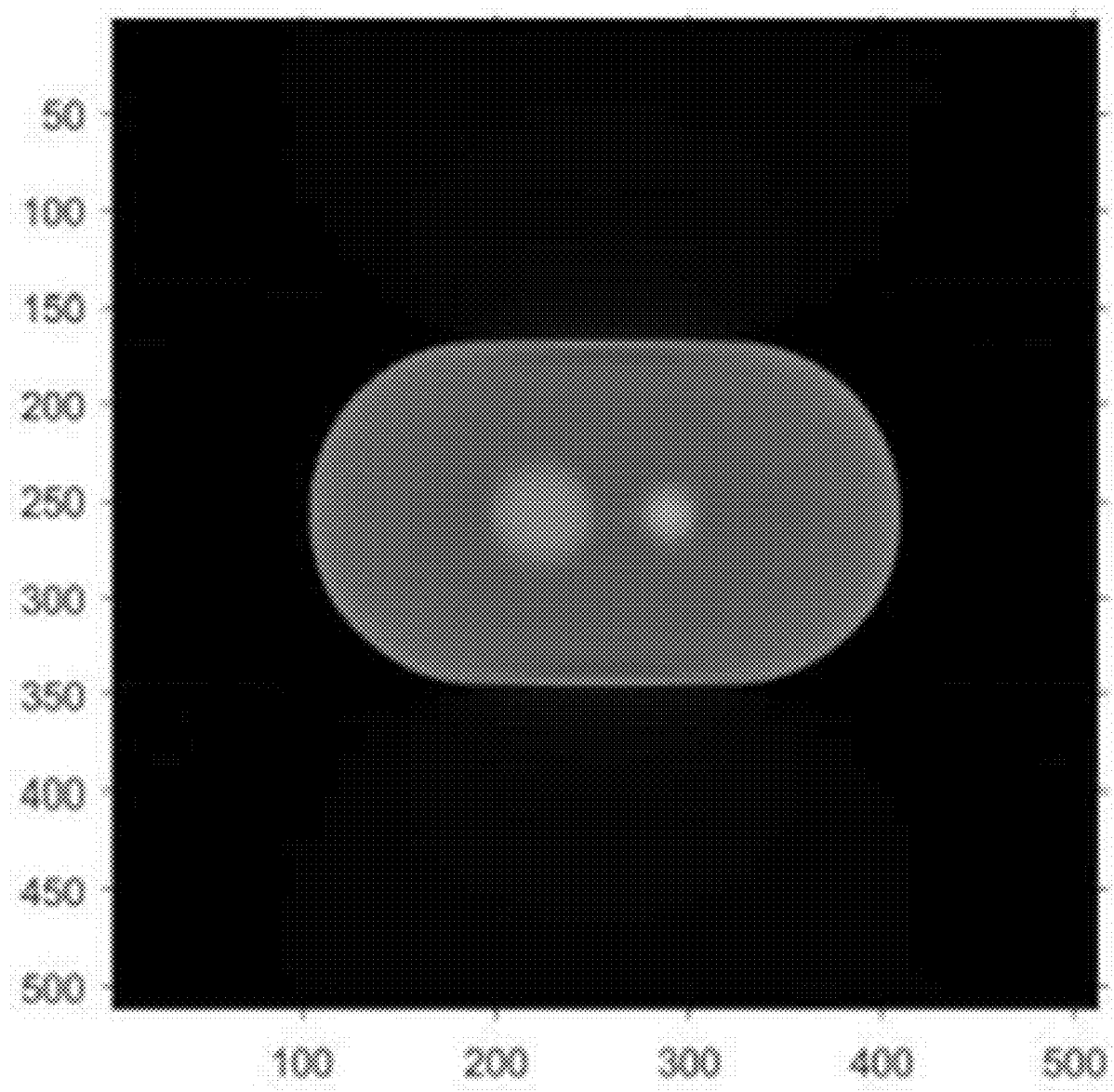
Figure 9B:
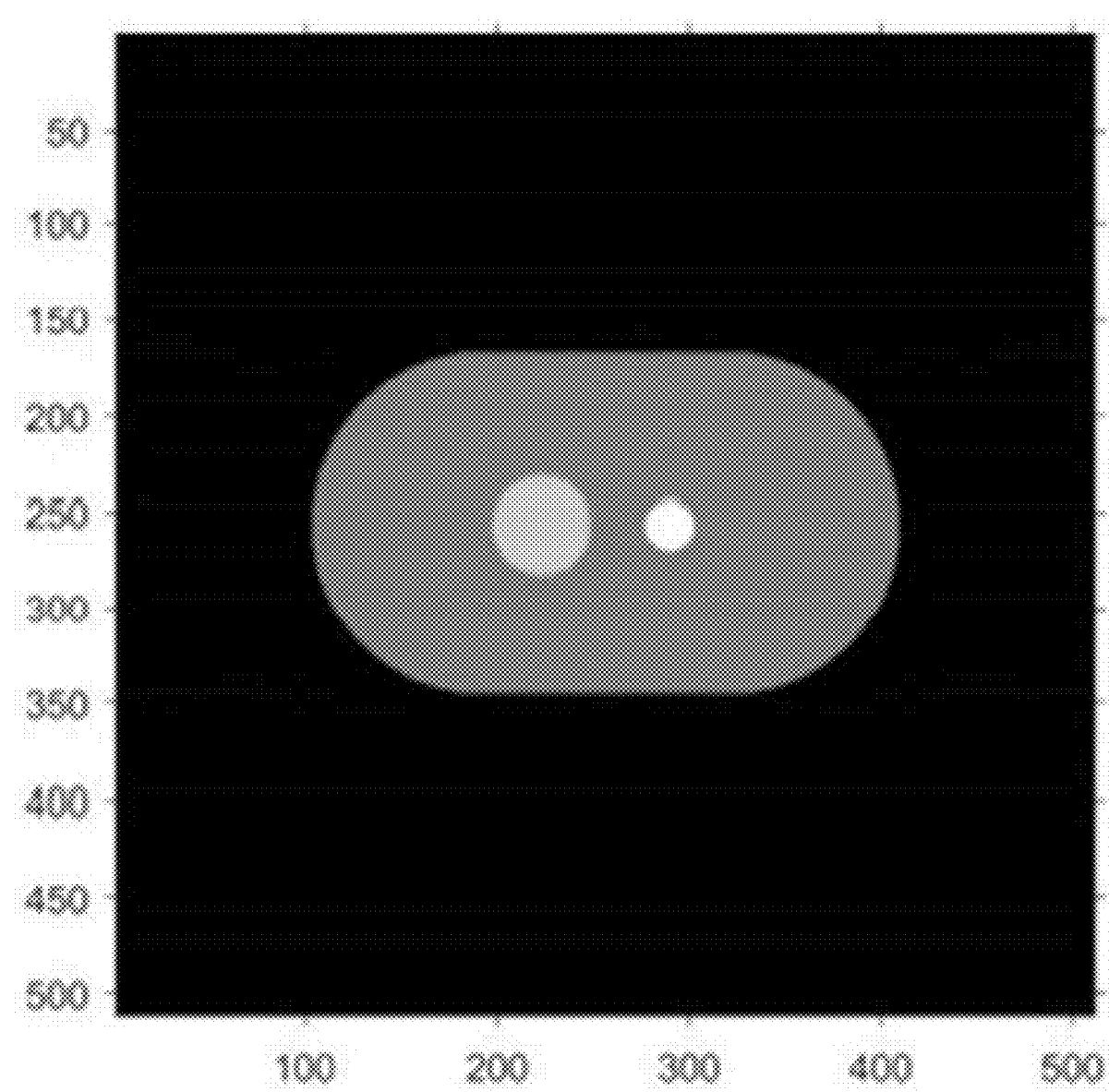
Figure 9C:
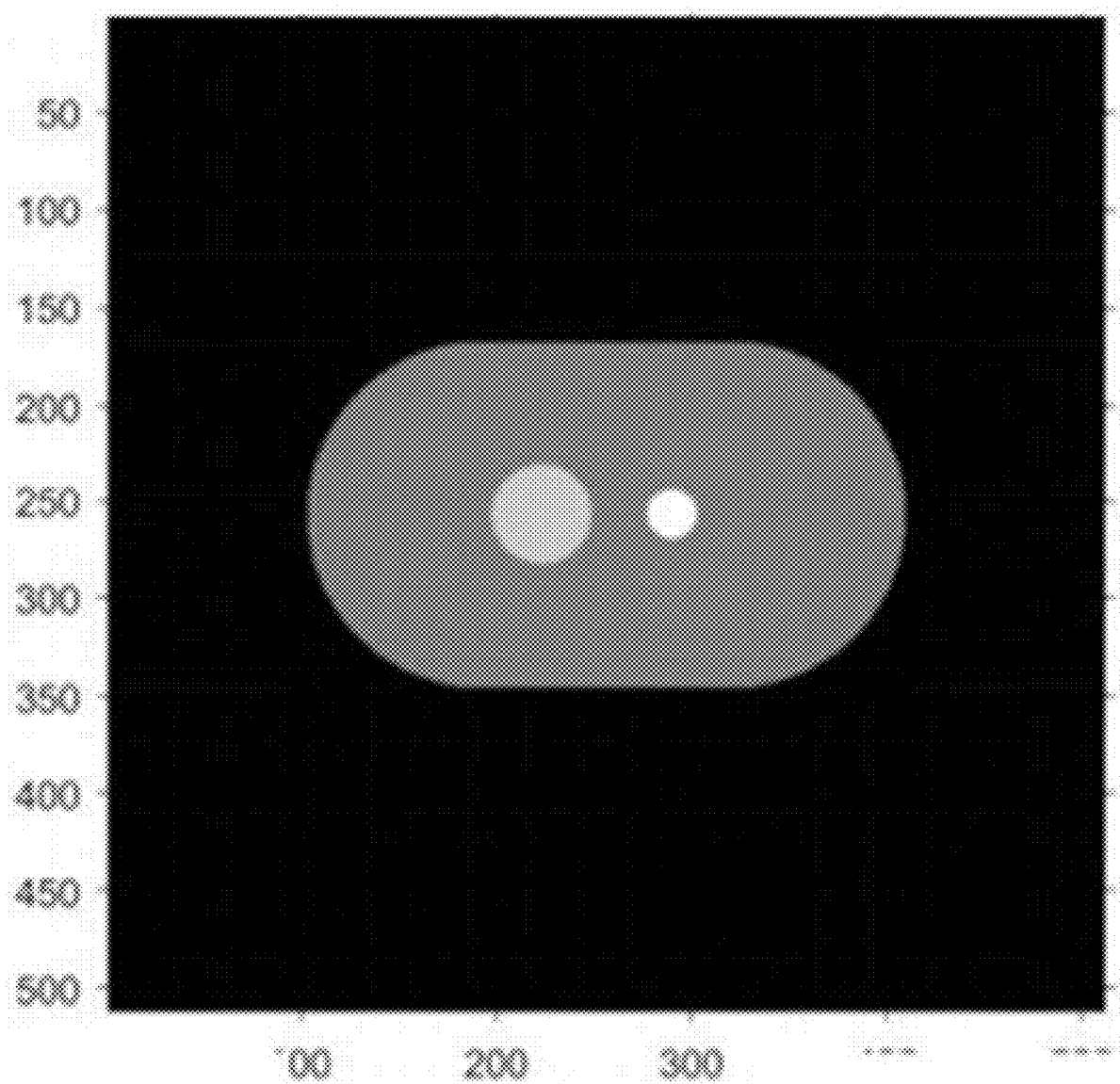
Figure 9D:
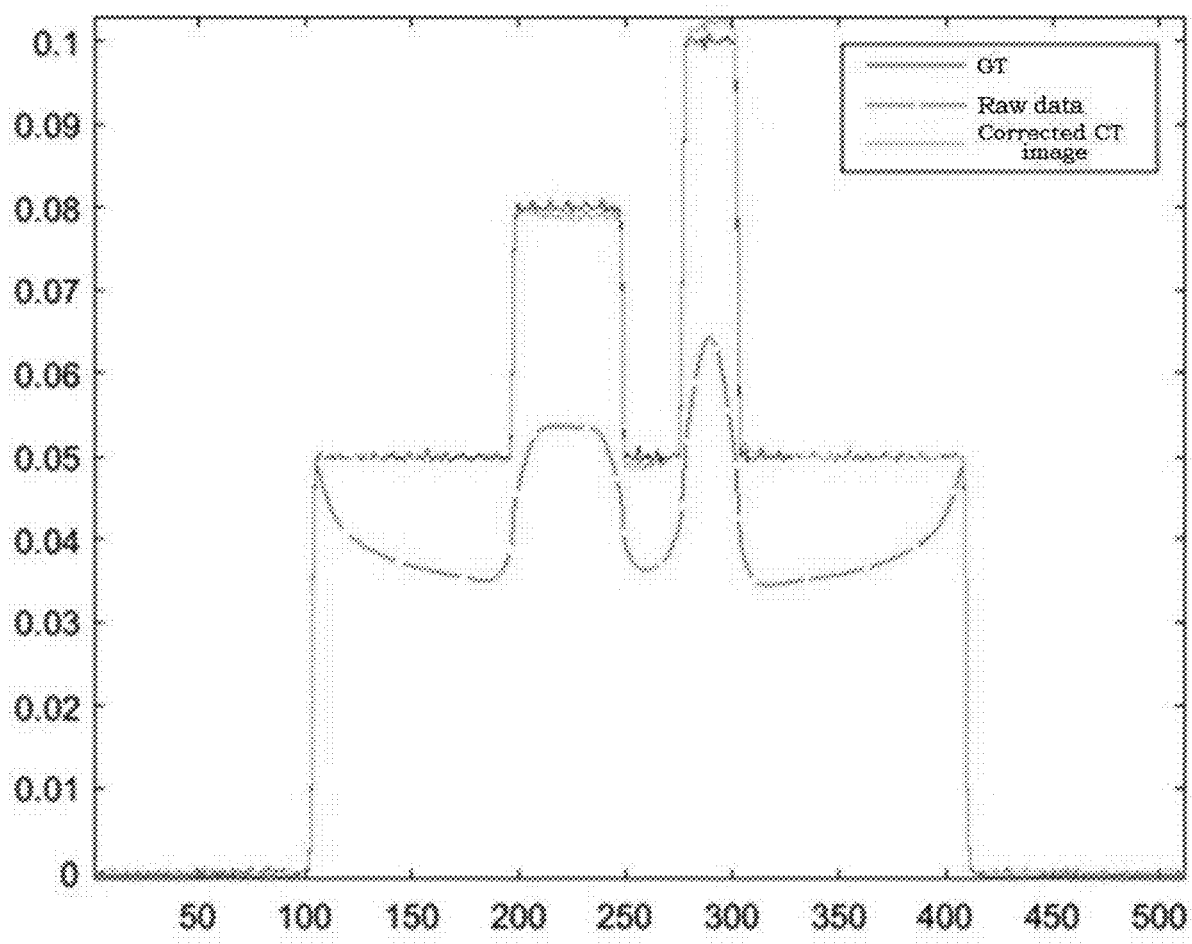
Figure 10A:
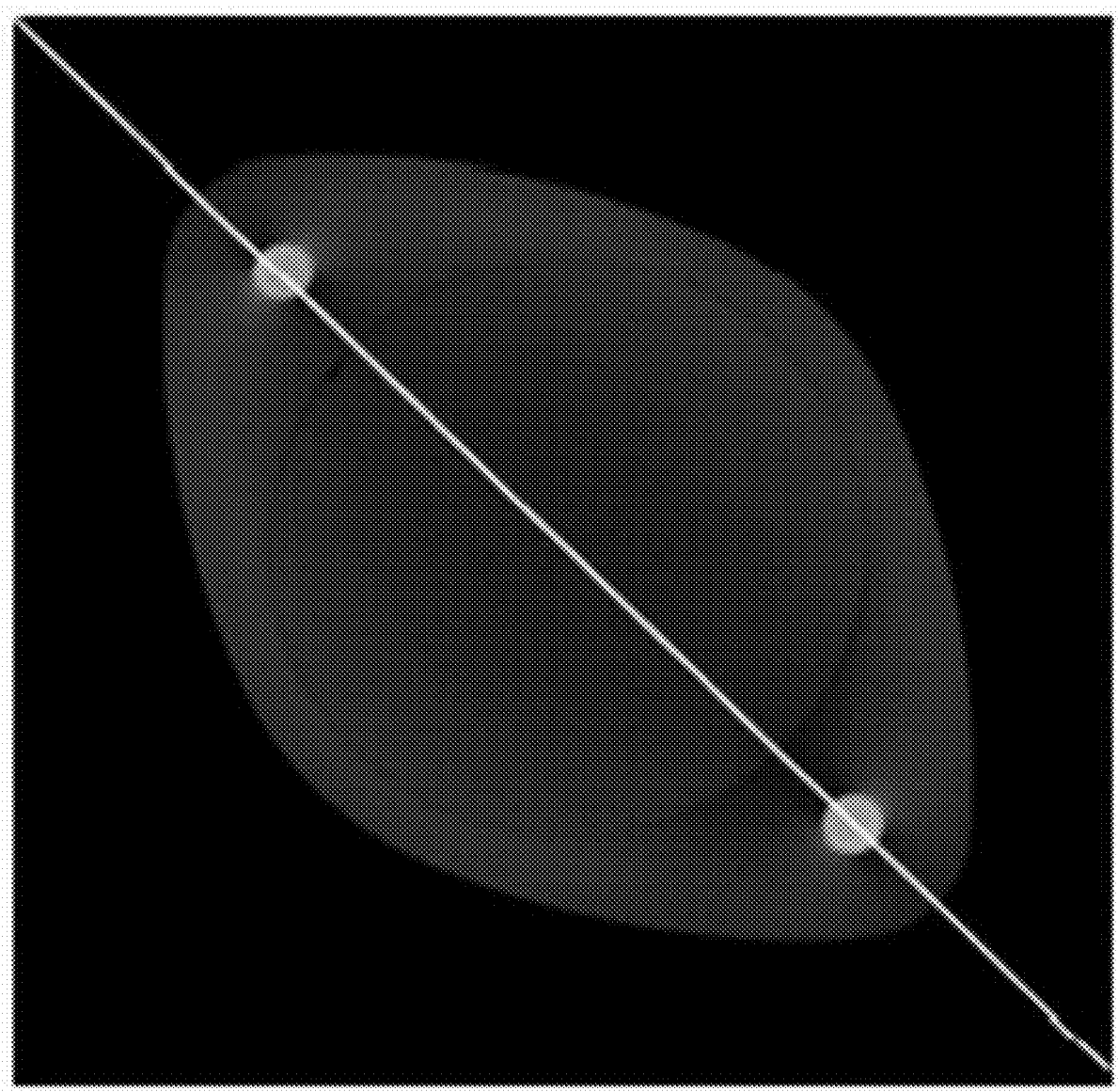
Figure 10B:
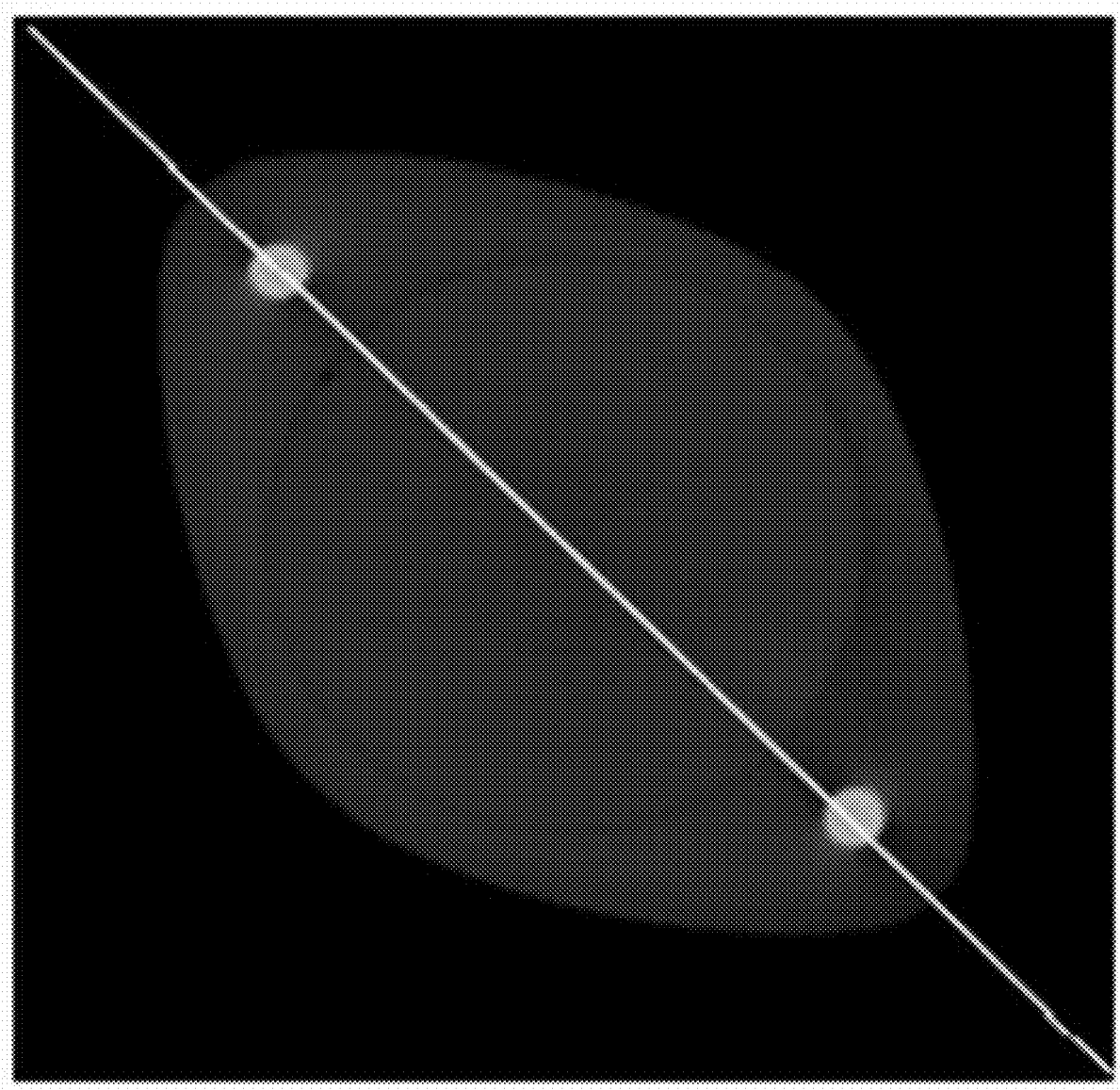
Figure 10C:
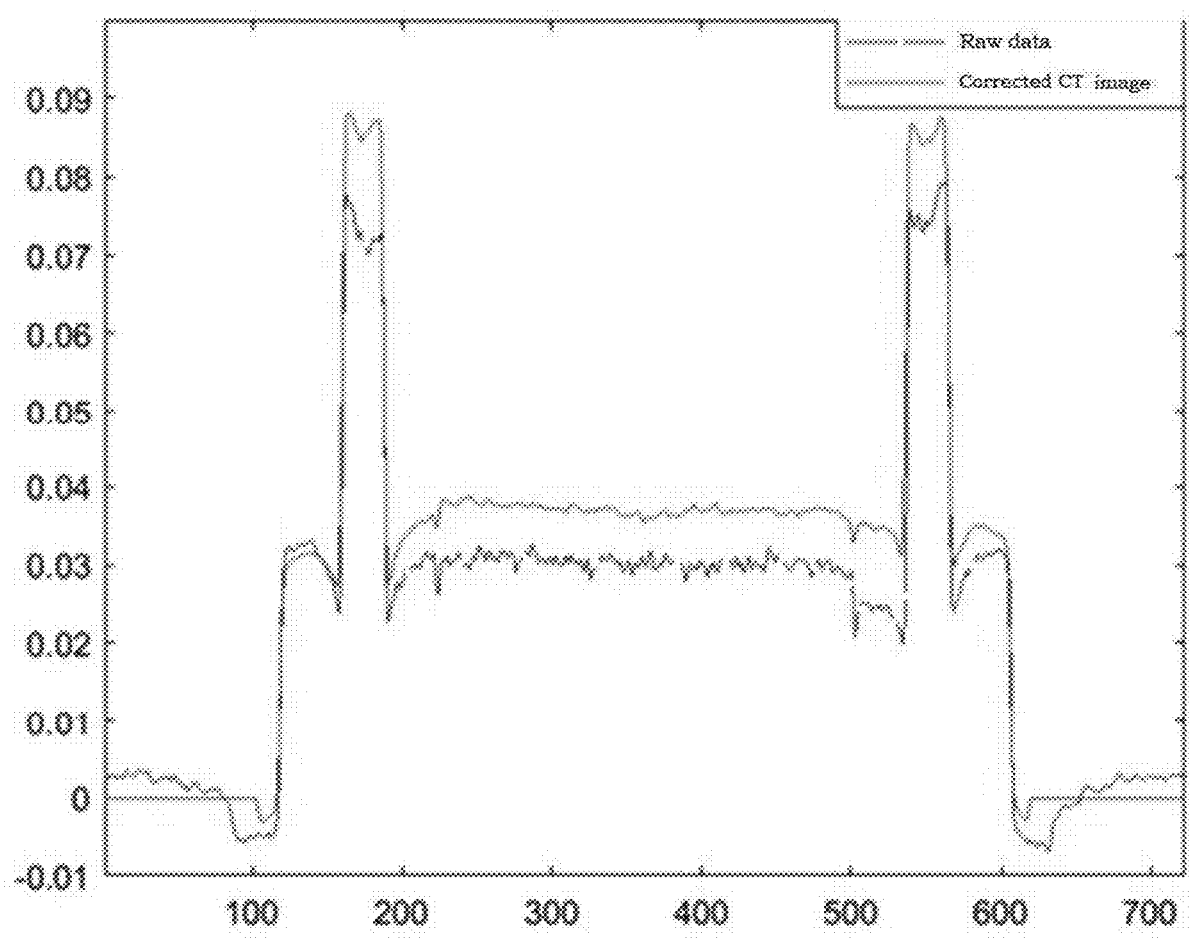

FIGS. 8A, 8B, 8C, 8D, 9A, 9B, 9C, 9D, 10A, 10B, and 10C illustrate examples of describing operation performance of the electronic device 100 according to example embodiments. FIGS. 8A, 9A, and 10A represent an example of raw data acquired from a subject and FIGS. 8B, 9B, and 10B represent an example of a corrected CT image from the raw data according to example embodiments. FIGS. 8C and 9C represent an example of a reference image (also referred to as ground truth (GT)) acquired from the subject without including a scattering effect. Here, although the reference image may be acquired through Monte-Carlo (MC) simulation, a relatively long period of time may be generally required for the MC simulation. FIGS. 10A, 10B, and 10C relate to an example of an actual CT image and there is no reference image. FIGS. 8D, 9D, and 10C may represent sharpness of a corrected CT image according to example embodiments.

Referring to FIGS. 8A, 8B, 8C, 8D, 9A, 9B, 9C, 9D, 10A, 10B, and 10C, the electronic device 100 according to example embodiments may effectively remove a scatter signal from raw data acquired from a subject. Here, the electronic device 100 may generate a sharp CT image that is very similar to the reference image. Here, the electronic device 100 estimated, from the raw data as illustrated in FIG. 8A, values (5.998e-04, −3.000e-01, 1.500e+00, 1.000e+01, 2.008e+00, 2.004e-04) of variables associated with the scatter kernel. The values are very similar to (6.000e-04, −3.000-e01, 1.500e+00, 1.000e+01, 2.000e+00, 2.004e-04) of variables associated with the scatter kernel with respect to the reference image as illustrated in FIG. 8C. Meanwhile, the electronic device 100 estimated, from the raw data as illustrated in FIG. 9A, values (9.9476e-04, −2.999e-01, 1.500e+00, 8.022e+00, 2.052e+00, 2.045e-04) of variables associated with the scatter kernel. The values are very similar to (10.000e-04, −3.000e-01, 1.500e+00, 8.000e+00, 2.000e+00, 2.004e-04) of variables associated with the scatter kernel with respect to the reference image as illustrated in FIG. 9C. It may represent that the electronic device 100 accurately estimates variables associated with the scatter kernel. Therefore, the electronic device 100 may verify that the scattering effect occurring in CT is efficiently corrected.

According to example embodiments, the electronic device 100 may efficiently estimate a scatter kernel by accurately estimating variables used to determine the scatter kernel. That is, the electronic device 100 may efficiently estimate the scatter kernel without an additional physical operation. In this manner, the electronic device 100 may effectively correct the scattering effect occurring in CT by removing, from raw data, a scatter signal estimated based on the scatter kernel. That is, the electronic device 100 may generate a sharp CT image with improved contrast that does not include the scattering effect.

The electronic device 100 according to example embodiments may include the data preparation module 110 configured to prepare raw data acquired from a subject through CT and a primary signal acquired from shape prior information of the subject, the scatter artifacts correction module 120 configured to estimate a scatter kernel based on the raw data and the primary signal and to acquire result data by removing, from the raw data, a scatter signal estimated based on the scatter kernel, and an image generation module, for example, the CT image generation module 130 of FIG. 1, configured to generate an image from the result data.

According to example embodiments, multiple variables may be defined to determine the scatter kernel.

According to example embodiments, the scatter artifacts correction module 120 may estimate the scatter kernel by estimating each variable separately.

According to example embodiments, the scatter artifacts correction module 120 may set at least one sub-variable among the variables to 0, may estimate main variables among the variables, may estimate the sub-variable based on the values of the main variables, and may estimate the scatter kernel based on the values of the main variables and the sub-variable.

According to example embodiments, the scatter artifacts correction module 120 may estimate the variables based on a minimization problem as in the above Equation 1.

According to example embodiments, when the scatter signal is defined as the above Equation 2, the variables may be defined as the group as represented as the above Equation 3.

According to example embodiments, B and $\sigma_2$ may be sub-variables, and A, $\alpha$, $\beta$ and $\sigma_1$ may be main variables.

According to example embodiments, the CT image generation module 130 may generate a sinogram from the result data, and may reconstruct the image based on the sinogram.

According to example embodiments, the shape prior information may be detected from CAD data that is acquired from the subject.

An operating method of the electronic device 100 according to example embodiments may include preparing raw data acquired from a subject through CT and a primary signal acquired from shape prior information of the subject; estimating a scatter kernel based on the raw data and the primary signal; acquiring result data by removing, from the raw data, a scatter signal estimated based on the scatter kernel; and generating an image from the result data.

According to example embodiments, multiple variables may be defined to determine the scatter kernel.

According to example embodiments, the estimating of the scatter kernel may include estimating the scatter kernel by estimating each variable separately.

According to example embodiments, the estimating of the scatter kernel may include setting at least one sub-variable among the variables to 0, estimating main variables among the variables, estimating the sub-variable based on the values of the main variables, and estimating the scatter kernel based on the values of the main variables and the sub-variable.

According to example embodiments, the estimating of the scatter kernel may include estimating the variables based on the minimization problem of the above Equation 4.

According to example embodiments, when the scatter signal is defined as the above Equation 5, the variables are defined as the following group of the above Equation 6.

According to example embodiments, B and $\sigma_2$ may be sub-variables, A, $\alpha$, $\beta$ and $\sigma_1$ may be main variables.

According to example embodiments, the generating of the image may include generating a sinogram from the result data, and reconstructing the image based on the sinogram.

According to example embodiments, the shape prior information may be detected from CAD data that is acquired from the subject.

The example embodiments disclosed herein may be implemented as software that includes one or more instructions stored in a storage medium readable by a machine, for example, the electronic device 100. For example, a processor of a device may call at least one of the instructions stored in the storage medium and may execute the called instruction. This enables the device to perform at least one function in response to the called at least one instruction. The at least one instruction may be executed by a code created by a compiler or a code executable by an interpreter. The machine-readable storage medium may be provided in a form of a non-transitory storage medium. Here, "non-transitory" simply represents that the storage medium is a tangible device and does not include a signal (e.g., an electromagnetic wave). This term does not distinguish between a case in which data is semi-permanently stored in a storage medium and a case in which data is temporarily stored.

The non-transitory computer-readable storage medium according to the example embodiments may store one or more program for executing an operation of preparing raw data acquired from a subject through CT and a primary signal acquired from shape prior information of the subject, estimating a scatter kernel based on the raw data and the primary signal, acquiring result data by removing, from the raw data, a scatter signal estimated based on the scatter kernel, and generating an image from the result data.

The electronic device according to the example embodiments disclosed herein may be various types of devices. The electronic devices may include, for example, a portable communication device (e.g., a smartphone), a computer device, a portable multimedia device, a portable medical device, a camera, a wearable device, and a home appliance. The electronic device according to the example embodiments is not limited to the aforementioned devices.

The example embodiments and the terms used herein are not construed to limit the technique described herein to specific example embodiments and may be understood to include various modifications, equivalents, and/or substitutions. Like reference numerals refer to like elements throughout. As used herein, the singular forms "a," "an," and "the," are intended to include the plural forms as well, unless the context clearly indicates otherwise. Herein, the expressions, "A or B," "at least one of A and/or B," "A, B, or C," "at least one of A, B, and/or C," and the like may include any possible combinations of listed items. Terms "first," "second," etc., are used to describe various components and the components should not be limited by the terms. The terms are simply used to distinguish one component from another component. When a component (e.g., a first component) is described to be "(functionally or communicatively) connected to" or "accessed to" another component (e.g., a second component), the component may be directly connected to the other component or may be connected through still another component (e.g., a third component).

The term "module" used herein may include a unit configured as hardware, software, or firmware, and may be interchangeably used with, for example, the terms "logic," "logic block," "part," "circuit," etc. The module may be an integrally configured part, a minimum unit that performs at least one function, or a portion thereof. For example, the module may be configured as an application-specific integrated circuit (ASIC).

According to the example embodiments, each of the components (e.g., module or program) may include a single object or multiple objects. According to the example embodiments, at least one of the components or operations may be omitted. Alternatively, at least one or more other components or operations may be added. Alternatively or additionally, multiple components (e.g., modules or programs) may be integrated into a single component. In this case, the integrated component may perform one or more functions of each component in the same or similar manner as is performed by the corresponding component before integration. According to the example embodiments, operations performed by a module, a program, or other components may be performed in a sequential, parallel, iterative, or heuristic manner. Alternatively, at least one of the operations may be performed in different sequence or omitted. Alternatively, at least one or more operations may be added.

While this disclosure includes specific example embodiments, it will be apparent to one of ordinary skill in the art that various alterations and modifications in form and details may be made in these example embodiments without departing from the spirit and scope of the claims and their equivalents. For example, suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An operating method of an electronic device, the method comprising:
   preparing raw data acquired from a subject through computed tomography (CT) and a primary signal acquired from shape prior information of the subject;
   estimating a scatter kernel based on the raw data and the primary signal;
   acquiring result data by removing, from the raw data, a scatter signal estimated based on the scatter kernel; and
   generating an image from the result data.

2. The method of claim 1, wherein multiple variables are defined to determine the scatter kernel, and
   wherein the estimating of the scatter kernel comprises estimating the scatter kernel by estimating each variable separately.

3. The method of claim 2, wherein the estimating of the scatter kernel comprises:
   setting at least one sub-variable among the variables to 0;
   estimating main variables among the variables;
   estimating the sub-variable based on the values of the main variables; and
   estimating the scatter kernel based on the values of the main variables and the sub-variable.

4. The method of claim 3, wherein the estimating of the scatter kernel comprises estimating the variables based on a minimization problem as in the following equation:

$$\min_x \| I - (\tilde{I}_p + \tilde{I}_s) \|^2$$

where the x denotes the variables, the I denotes the raw data, the $\tilde{I}_p$ denotes the primary signal, and the $\tilde{I}_s$ denotes the scatter signal estimated based on the scatter kernel.

5. The method of claim 4, wherein, when the scatter signal is defined as the following equation:

$$\tilde{I}_s(x, y) = (\tilde{I}_p(x, y) A_f(x, y)) * h_s(x, y),$$

$$A_f = A \cdot \left( \frac{\tilde{I}_p(x, y)}{I_0(x, y)} \right)^\alpha \cdot \left( \ln\left( \frac{I_0(x, y)}{\tilde{I}_p(x, y)} \right) \right)^\beta,$$

and $$h_s = \left[ \exp\left( \frac{-r^2}{2\sigma_1^2} \right) + B \exp\left( \frac{-r^2}{2\sigma_2^2} \right) \right],$$

the variables are defined as the following group:
   $x = (A, \alpha, \beta, \sigma_1, B, \sigma_2)$.

6. The method of claim 5, wherein each of the B and the $\sigma_2$ denotes the sub-variable, and
   the A, the $\alpha$, the $\beta$, and the $\sigma_1$ denote the main variables.

7. The method of claim 1, wherein the generating of the image comprises:
   generating a sinogram from the result data; and
   reconstructing the image based on the sinogram.

8. The method of claim 1, wherein the shape prior information is detected from computer-aided design (CAD) data that is acquired from the subject.

9. An electronic device comprising:
   a data preparation module configured to prepare raw data acquired from a subject through computed tomography (CT) and a primary signal acquired from shape prior information of the subject;
   a scatter artifacts correction module configured to estimate a scatter kernel based on the raw data and the primary signal and to acquire result data by removing, from the raw data, a scatter signal estimated based on the scatter kernel; and
   an image generation module configured to generate an image from the result data.

10. The electronic device of claim 9, wherein multiple variables are defined to determine the scatter kernel, and
    the scatter artifacts correction module is configured to estimate the scatter kernel by estimating each variable separately.

11. The electronic device of claim 10, wherein the scatter artifacts correction module is configured to
    set at least one sub-variable among the variables to 0,
    estimate main variables among the variables,
    estimate the sub-variable based on the values of the main variables, and
    estimate the scatter kernel based on the values of the main variables and the sub-variable.

12. The electronic device of claim 11, wherein the scatter artifacts correction module is configured to estimate the variables based on a minimization problem as in the following equation:

$$\min_x \| I - (\tilde{I}_p + \tilde{I}_s) \|^2$$

where the x denotes the variables, the I denotes the raw data, the $\tilde{I}_p$ denotes the primary signal, and the $\tilde{I}_s$ denotes the scatter signal estimated based on the scatter kernel.

13. The electronic device of claim 12, wherein, when the scatter signal is defined as the following equations:

$$\tilde{I}_s(x, y) = (\tilde{I}_p(x, y) A_f(x, y)) * h_s(x, y),$$

$$A_f = A \cdot \left( \frac{\tilde{I}_p(x, y)}{I_0(x, y)} \right)^\alpha \cdot \left( \ln\left( \frac{I_0(x, y)}{\tilde{I}_p(x, y)} \right) \right)^\beta,$$

and $$h_s = \left[ \exp\left( \frac{-r^2}{2\sigma_1^2} \right) + B \exp\left( \frac{-r^2}{2\sigma_2^2} \right) \right],$$

the variables are defined as the following group:

$$x=(A,\alpha,\beta,\sigma_1,B,\sigma_2).$$

14. The electronic device of claim 13, wherein each of the B and the $\sigma_2$ denotes the sub-variable, and the A, the $\alpha$, the $\beta$, and the $\sigma_1$ denote the main variables.

15. The electronic device of claim 9, wherein the image generation module is configured to generate a sinogram from the result data, and reconstruct the image based on the sinogram.

16. The electronic device of claim 9, wherein the shape prior information is detected from computer-aided design (CAD) data that is acquired from the subject.

17. A non-transitory computer-readable record medium storing at least one program to perform a method comprising:

preparing raw data acquired from a subject through computed tomography (CT) and a primary signal acquired from shape prior information of the subject;

estimating a scatter kernel based on the raw data and the primary signal;

acquiring result data by removing, from the raw data, a scatter signal estimated based on the scatter kernel; and generating an image from the result data.

18. The non-transitory computer-readable record medium of claim 17, wherein multiple variables are defined to determine the scatter kernel, and wherein the operation of estimating the scatter kernel comprises estimating the scatter kernel by estimating each variable separately.

19. The non-transitory computer-readable record medium of claim 18, wherein the estimating of the scatter kernel comprises:

setting at least one sub-variable among the variables to 0;

estimating main variables among the variables;

estimating the sub-variable based on the values of the main variables; and estimating the scatter kernel based on the values of the main variables and the sub-variable.

20. The non-transitory computer-readable record medium of claim 19, wherein the estimating of the scatter kernel comprises estimating the variables based on a minimization problem as in the following equation:

$$\min_x \left\| I - (\tilde{I}_p + \tilde{I}_s) \right\|^2$$

where the x denotes the variables, the I denotes the raw data, the $\tilde{I}_p$ denotes the primary signal, and the $\tilde{I}_s$ denotes the scatter signal estimated based on the scatter kernel.

* * * * *